United States Patent [19]
Jacobs et al.

[11] Patent Number: 5,489,259
[45] Date of Patent: Feb. 6, 1996

[54] PRESSURE-NORMALIZING SINGLE-CHAMBERED STATIC PRESSURE DEVICE FOR SUPPORTING AND PROTECTING A BODY EXTREMITY

[75] Inventors: Kerry L. Jacobs, Mooresville; Roy E. Reed, Plainfield, both of Ind.; William Purdy, White Plains, N.Y.; Jeffrey B. Quillen, Richmond, Ind.

[73] Assignee: Sundance Enterprises, Inc., Mooresville, Ind.

[21] Appl. No.: 144,139

[22] Filed: Oct. 27, 1993

[51] Int. Cl.⁶ ......................................................... A61F 5/00
[52] U.S. Cl. .................... 602/13; 602/27; 602/14; 128/882; 128/DIG. 20
[58] Field of Search .................... 602/5, 13, 14, 602/23, 27, 61, 62, 65; 128/882, DIG. 20

[56] References Cited

U.S. PATENT DOCUMENTS

| | | |
|---|---|---|
| 585,834 | 7/1897 | Ruth . |
| 1,666,846 | 4/1928 | Cooper . |
| 1,726,939 | 9/1929 | Anderson . |
| 2,028,060 | 1/1936 | Gilbert . |
| 2,247,961 | 7/1941 | Mulvey . |
| 2,267,070 | 12/1941 | Baldwin .................... 602/62 X |
| 2,638,606 | 5/1953 | Austin . |
| 2,651,302 | 9/1953 | Berry . |
| 2,657,385 | 11/1953 | Cushman et al. . |
| 2,759,186 | 8/1956 | Dye . |
| 2,823,668 | 2/1958 | Van Court et al. . |
| 2,842,783 | 7/1958 | Druck . |
| 2,943,859 | 7/1960 | Koski et al. . |
| 2,987,114 | 6/1961 | Klepper . |
| 3,074,398 | 1/1963 | Guiney . |
| 3,164,152 | 1/1065 | Nicoll . |
| 3,186,405 | 6/1965 | Bailey et al. . |
| 3,217,333 | 11/1965 | Sweet et al. . |
| 3,338,237 | 8/1967 | Sconce . |
| 3,351,055 | 11/1967 | Gottfried . |
| 3,550,159 | 12/1970 | Alarco . |
| 3,561,435 | 2/1971 | Nicholson . |
| 3,610,235 | 10/1971 | Vagacs . |

(List continued on next page.)

FOREIGN PATENT DOCUMENTS

| | | |
|---|---|---|
| 440113 | 1/1927 | Germany . |
| 1171361 | 11/1969 | United Kingdom . |
| 2016905 | 10/1979 | United Kingdom . |

OTHER PUBLICATIONS

Adapt II™ Air Support System Brochure.
Original Foot Waffle® Advertising Brochure by EHOB, Inc. ©1993 EHOB®, Inc. (4 pages).
New Foot Waffle® Advertising Bulletin by EHOB, Inc. ©1993 EHOB®, Inc. (3 pages).
Instructions for use of original Foot Waffle® ©1993 EHOB, Inc. (1 page).
Foot Waffle® Advertisement ©1993 EHOB, Inc. (1 page).

*Primary Examiner*—Linda C. M. Dvorak
*Attorney, Agent, or Firm*—Willian Brinks Hofer Gilson & Lione

[57] ABSTRACT

A single-chambered static pressure device and method for supporting and protecting a human lower extremity and for normalizing the pressure and forces acting thereon includes an inflatable wrap or boot-like device having a single internal air chamber and including an interior plastic sheet and an exterior plastic sheet joined peripherally together forming said air chamber therebetween, a nozzle valve for admitting air into the air chamber, and fasteners for releasably securing the inflatable device about the lower extremity. The plastics sheets forming the single air chamber have a plurality of aligned openings extending therethrough and the sheets are joined about the circumference of each hole for providing heat and moisture dissipation, ventilation and visibility therethrough. The device is disposed in an under-inflated state about the lower extremity to allow the interior surface of the device to engage and conform to the contour of said lower limb during inflation to normalize the pressure applied to the extremity at the interface between the device and the surface of the lower extremity to prevent and better manage pressure sores and other lower extremity pathologies.

39 Claims, 11 Drawing Sheets

U.S. PATENT DOCUMENTS

| | | |
|---|---|---|
| 3,685,176 | 8/1972 | Rudy . |
| 3,758,964 | 9/1973 | Nishimura . |
| 3,771,519 | 11/1973 | Haake . |
| 3,784,985 | 1/1974 | Conroy . |
| 3,786,805 | 1/1974 | Tourin . |
| 3,804,085 | 4/1974 | Eshuis et al. . |
| 3,854,228 | 12/1974 | Conroy . |
| 3,877,077 | 4/1975 | Chapdelaine . |
| 3,930,496 | 1/1976 | Gibbons . |
| 3,995,320 | 12/1976 | Zafuto . |
| 4,071,031 | 1/1978 | Lowman . |
| 4,142,252 | 3/1979 | Storer . |
| 4,157,713 | 6/1979 | Clarey . |
| 4,197,845 | 4/1980 | Browning . |
| 4,213,202 | 7/1980 | Larry . |
| 4,263,905 | 4/1981 | Couch, Jr. . |
| 4,266,298 | 5/1981 | Graziano . |
| 4,399,815 | 8/1983 | Bachorik . |
| 4,624,248 | 11/1986 | Poole et al. . |
| 4,639,960 | 2/1987 | Quillen et al. . |
| 4,685,163 | 8/1987 | Quillen et al. . |
| 4,730,610 | 3/1988 | Graebe . |
| 4,805,601 | 2/1989 | Eishen, Sr. ................ 601/151 |
| 4,841,957 | 6/1989 | Wooten et al. . |
| 4,938,208 | 7/1990 | Dye . |
| 5,025,575 | 6/1991 | Lakic .......................... 36/44 |
| 5,085,214 | 2/1992 | Barrett . |
| 5,086,771 | 2/1992 | Molloy ................. 128/892 X |
| 5,111,807 | 5/1992 | Spahn et al. . |
| 5,125,400 | 6/1992 | Johnson, Jr. . |
| 5,218,954 | 6/1993 | van Bemmelen . |
| 5,226,245 | 7/1993 | Lamont . |
| 5,265,293 | 11/1993 | Spahn et al. . |
| 5,288,286 | 2/1994 | Davis et al. ................ 602/6 |
| 5,328,445 | 7/1994 | Spahn et al. ............... 602/13 |

PRESSURE-NORMALIZING SINGLE-CHAMBERED STATIC PRESSURE DEVICE FOR SUPPORTING AND PROTECTING A BODY EXTREMITY

FIELD OF THE INVENTION

This invention relates to medical devices intended for use with body extremities and, more particularly, to an air pressurizable supportive and protective device securable to a lower extremity of a patient to normalize and reduce the pressures and forces acting thereon to maintain sufficient blood flow circulation to the soft tissues, thereby preventing and aiding in the healing of pressure sores and other lower extremity pathologies.

BACKGROUND OF THE INVENTION

Medical devices used to immobilize and support various parts of the human body are known. This invention is directed to inflatable devices for supporting, protecting and normalizing the forces acting on body extremity, preferably a lower extremity, i.e. calf, ankle, Achilles, heel and foot regions, particularly for bedridden patients or those often confined in a supine position. A primary object is to reduce point pressures and heat and moisture build-up to maintain or improve the blood flow to the soft tissues of the lower extremity by normalizing the forces acting thereon to prevent the formation, and aid in the healing, of various pressure sores and other pathologies, including decubitus ulcers, commonly known as bed sores. Any region of a limb that experiences undue pressure or force to an extent that skin and soft tissue blood supply is compromised risks skin and soft tissue breakdown and maceration and the possible formation of decubitus ulcers and other related pressure sores. This tendency is even a greater risk for diabetics and those with vascular compromise.

One prior art attempt at protecting a lower limb discloses a multi-chambered air pressurizable boot manufactured by Ehob, Inc., Indianapolis, Ind., and commercially distributed under the trademark FOOT WAFFLE®. Multi-chambered systems have not proven satisfactory because the separate pressurized chambers prevent the displacement of the interior air volume of the device from a region of high pressure to a region of low pressure to thereby normalize and evenly distribute pressure applied by the device to the limb and the effect of gravity acting on the limb.

Thus, a need exists for means that satisfactorily normalizes and dissipates the pressure and forces acting on an extremity.

SUMMARY OF THE INVENTION

This invention provides an improved method and article providing protection, support and pressure normalization to a human limb, particularly a lower extremity.

The article provided by this invention is an air pressurizable boot- or wrap-like device having an open front portion intended, while in an underinflated state, to be fitted over to partially enclose a lower extremity in a cradle-like fashion. During air pressurization, the device conforms to the contour of the limb to normalize the forces acting upon the limb and maintain proper skin and soft tissue blood supply to that region of the body. Such a device can comprise an inflatable member having an interior surface and an exterior surface forming a single static pressure air chamber, means for releasably securing the inflatable member about the limb, and valve means carried by the member allowing for its inflation. The inflatable member is provided with an upper portion for engaging an upper region of the limb, an intermediate portion for engaging an intermediate region of the limb, and a lower portion for engaging a lower region of the limb. The intermediate portion can further include a cut-out portion for receiving therein the heel of the lower limb to allow total suspension of the heel.

The interior and exterior surfaces of the device are preferably defined by a pair of sheets joined together at their peripheries to form the single air chamber. The surfaces further have a plurality of aligned openings extending therethrough to provide ventilation and visibility therethrough with the sheets being joined together about the circumference of each opening.

When the limb is placed in a cradling fashion within the device, the device partially encloses the limb by covering the rear and side portions of the upper region while leaving the forwardly facing area exposed. Similarly, the protective device covers the rear and sides of the intermediate region and the bottom of the lower region, while leaving exposed the top portions of the intermediate and lower regions.

The pressure-normalizing protective device of this invention can further include a continuous or extended air bladder extension affixed to a forward edge of one side of the upper portion of the inflatable member adapted to be folded over to protect the shin area from breakdown due to maceration or undue pressures caused by localized insult.

The securing means provided by this invention can take several forms but preferably includes means having a pressure relief safety feature. Such means can include one or more straps attached to one side of the upper portion of the device and designed to extend toward and be secured at their distal ends to the opposing side of the upper portion of the device. Each strap can be provided with one component of a hook-and-loop type fastening means (commonly referred to as VELCRO®) and a corresponding number of the other component of such fastening means can be affixed to the opposite side of the upper portion of the device for releasably securing the straps. When the continuous extension air bladder is included in the embodiment, the air bladder is initially folded over the exposed shin area and then the one or more straps are pulled thereover and releasably secured.

The pressure-normalizing protective device of this invention preferably has a low internal static air pressure of no more than about 0.50 p.s.i., which is sufficient to dissipate and evenly distribute the pressure applied by the device to the limb at the common interface surfaces therebetween (hereinafter referred to as the "interface pressure"), as well as other forces acting on the limb. The interface pressure between the interior surface of the inflatable member and the surface of the limb can be further regulated by the extent to which the inflatable member is inflated, as well as by the extent to which the securing straps are tightened or loosened. Through the combined action of the ability to regulate the inflation of the device and to selectively adjust the securing means, the device can be custom fitted to limbs of varying sizes and shapes.

The low internal static pressure of the inflatable member allows it during inflation to engage and conform to the contour of the limb which concomitantly maximizes the surface area contact between the device and the lower limb, thereby reducing the overall interface pressure at any one point or area about the lower limb. It is primarily the lack of impediments to the displacement of the large internal low-pressure air volume contained within its single chamber that enables the device of this invention to normalize, dissipate and evenly distribute any forces and pressures acting on any one area of the lower limb to achieve a reduced uniform distribution of pressure all about the limb. In conventional devices, for example, it is common that undue pressure, or simply the weight of the limb itself, is exerted on one area of the limb, particularly the heel and Achilles region, thereby compromising blood circulation to that area and inviting skin and soft tissue breakdown or the formation of pressure sores or other pathologies.

A single chamber static air design provided by this invention allows for a true low-pressure, pressure normalizing system which cannot be as easily achieved with a device having multiple chambers. With the single chamber device of this invention, the overall pressure applied to the limb may be reduced by the large volume displacement within its single internal air chamber. This further reduces the tangential or shear forces about the lower limb, thereby reducing the tendency of the limb to move relative to the device while secured therein.

This invention further provides a method of supporting and protecting a limb and normalizing the pressure and forces acting thereon, generally comprising providing an air-pressurizable device similar to that discussed above in an underinflated state and arranging the device about the limb in a cradle-like fashion, inflating the device to the extent that the interior of the device engages and conforms to the contour of the limb, and securing the device about the limb.

Other features and advantages of the invention will be apparent from the drawings and a more detailed description that follows.

DESCRIPTION OF THE PREFERRED EMBODIMENTS

Figure 1:
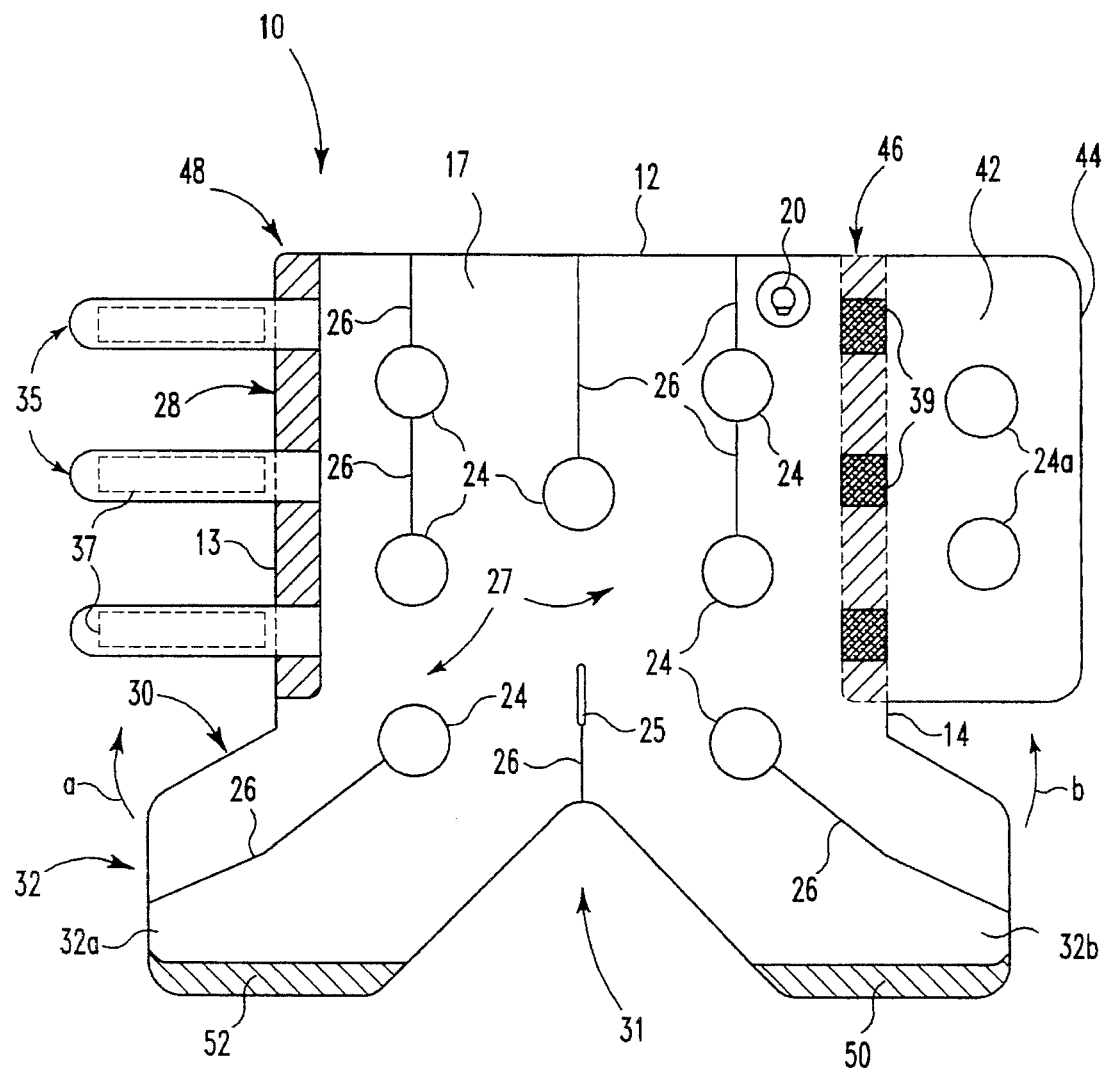
FIG. 1 is a flat plan view of a protective device provided by this invention in an underinflated, unassembled state for purposes of illustration.
Figure 2:
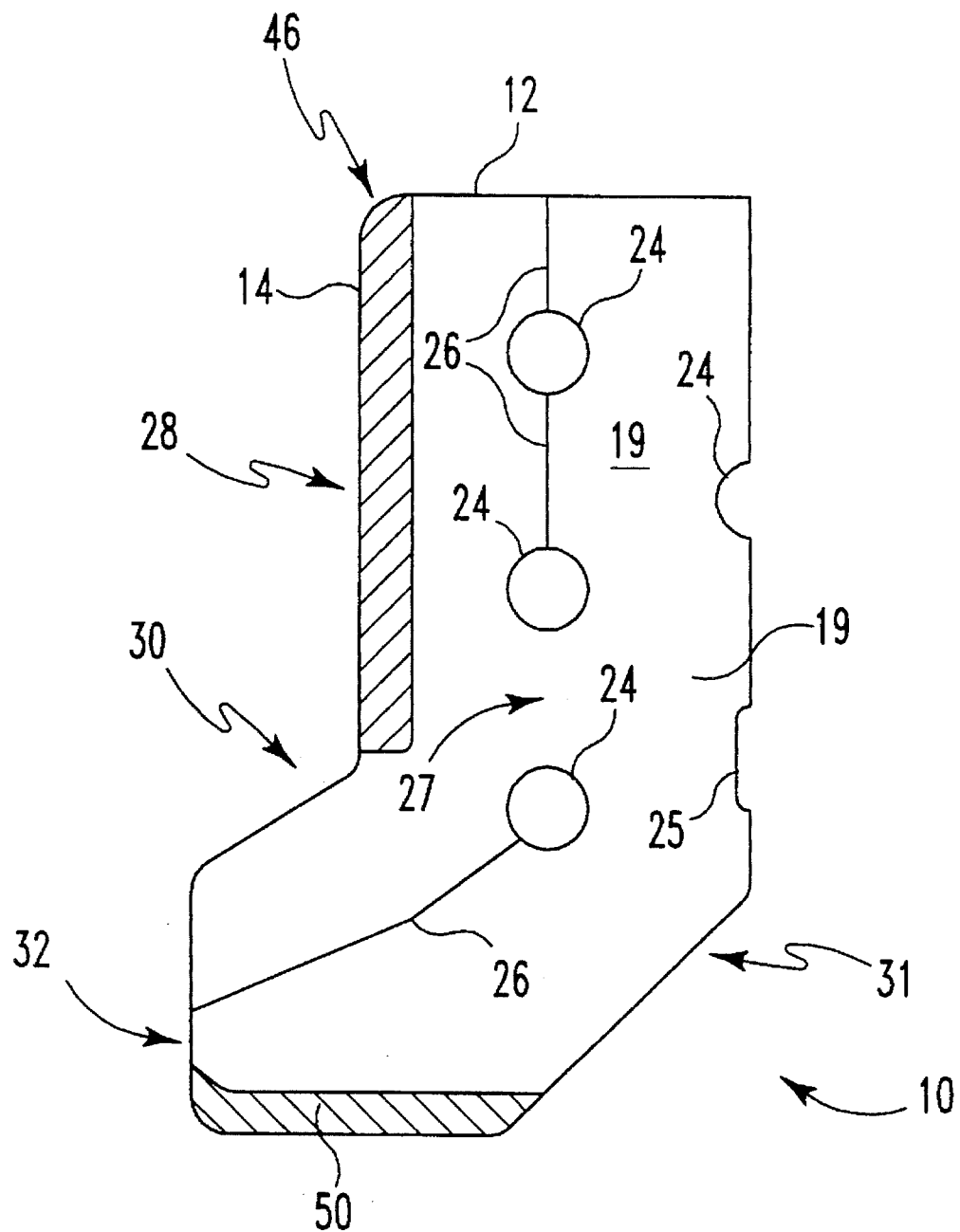
FIG. 2 is a partial flat plan view of the reverse side of the device of FIG. 1 in an underinflated state.

FIG. 1 shows a presently preferred embodiment of a pressure-normalizing protective device 10 provided by this invention in a underinflated, substantially flat and unassembled state for purposes of illustration. In FIG. 1, the exterior or outwardly facing side of device 10 is shown, but the device 10 is not fully assembled in that the mirror-image right and left sides of the device 10 have not been folded toward one another and joined at their lower bottom margins 50 and 52, respectively, by conventional heat sealing and plastic welding methods to form a boot-like device as shown in FIGS. 4–11. FIG. 2 shows a partial flat view of only half of the reverse or interior side of device 12 as shown in FIG. 1. FIGS. 4–7 show protective device 10 in a fully assembled and inflated, ready-to-use, state.

Protective device 10 is intended to receive therein and partially enclose in a cradling fashion a human limb and conform to the contour of the limb to normalize the interface pressure between the device and the surface of the limb to protect the limb and to maintain a proper blood supply to the soft tissues thereof prevent the formation of and facilitate the healing of pressure sores and other types of medical pathologies. While the discussion that follows will make reference to a lower extremity, this invention is applicable to various body extremities.

Protective device 10 can include an inflatable boot- or wrap-like member 12 having an interior surface and an exterior surface forming a single chamber static pressure member, air inflation means defined by a recessed one-way air valve 20 heat sealed into the exterior surface allowing inflation of member 12, and means for releasably securing the inflatable member 12 about the lower limb including, preferably, one or more straps 35 and hook-and-loop type fasteners 37 and 39.

Protective device 10 further includes an upper portion 28 for engaging and partially enclosing the calf region of the lower limb (see FIGS. 8–10), an intermediate portion 30 for engaging and partially enclosing the ankle and Achilles tendon region of the lower limb, and a lower portion 32 for engaging and partially enclosing the foot region of the lower limb.

Figure 7:
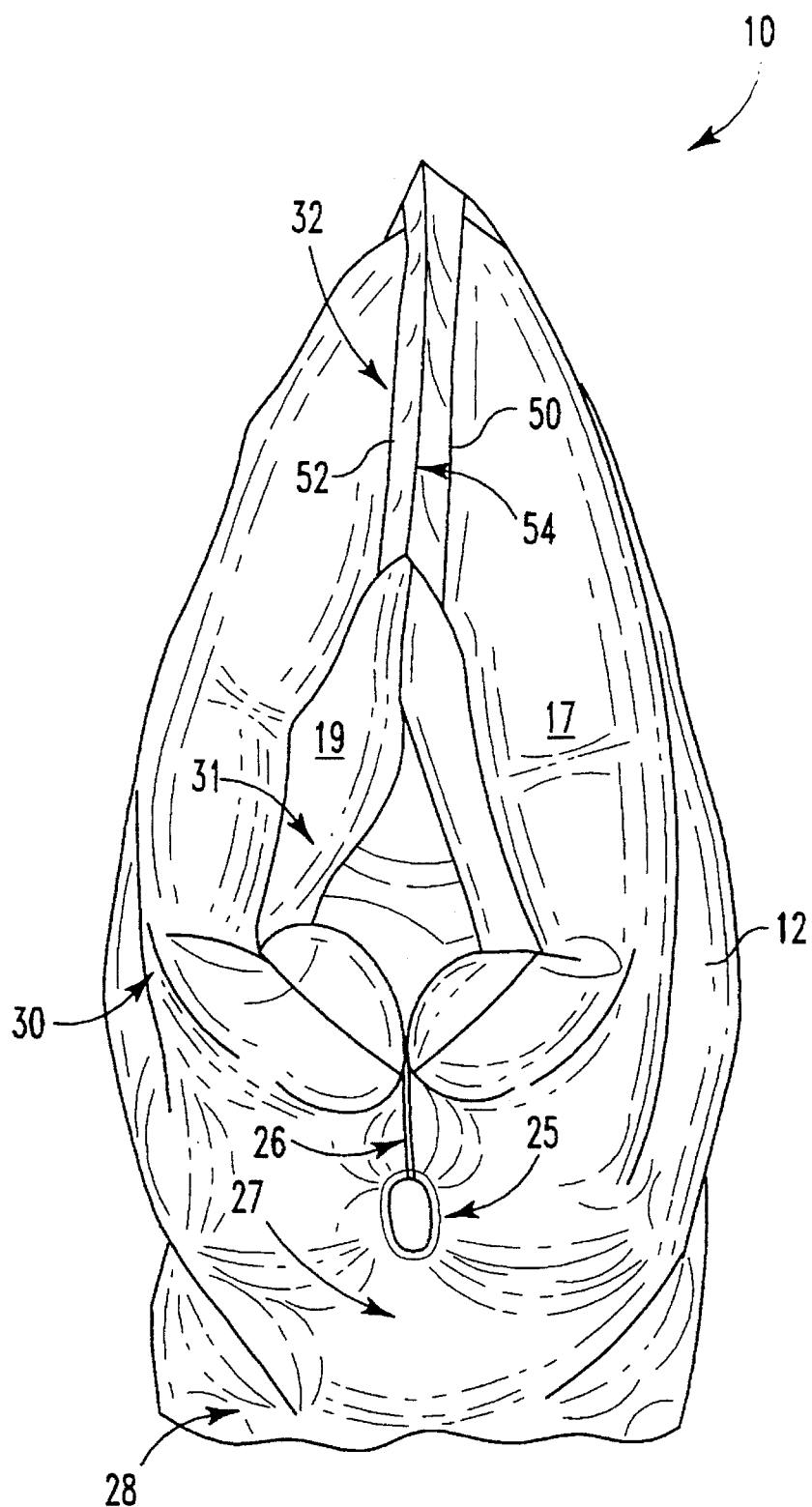
FIG. 7 is an isolated enlarged perspective view of a heel-receiving cut-out portion of the device.
Figure 11:
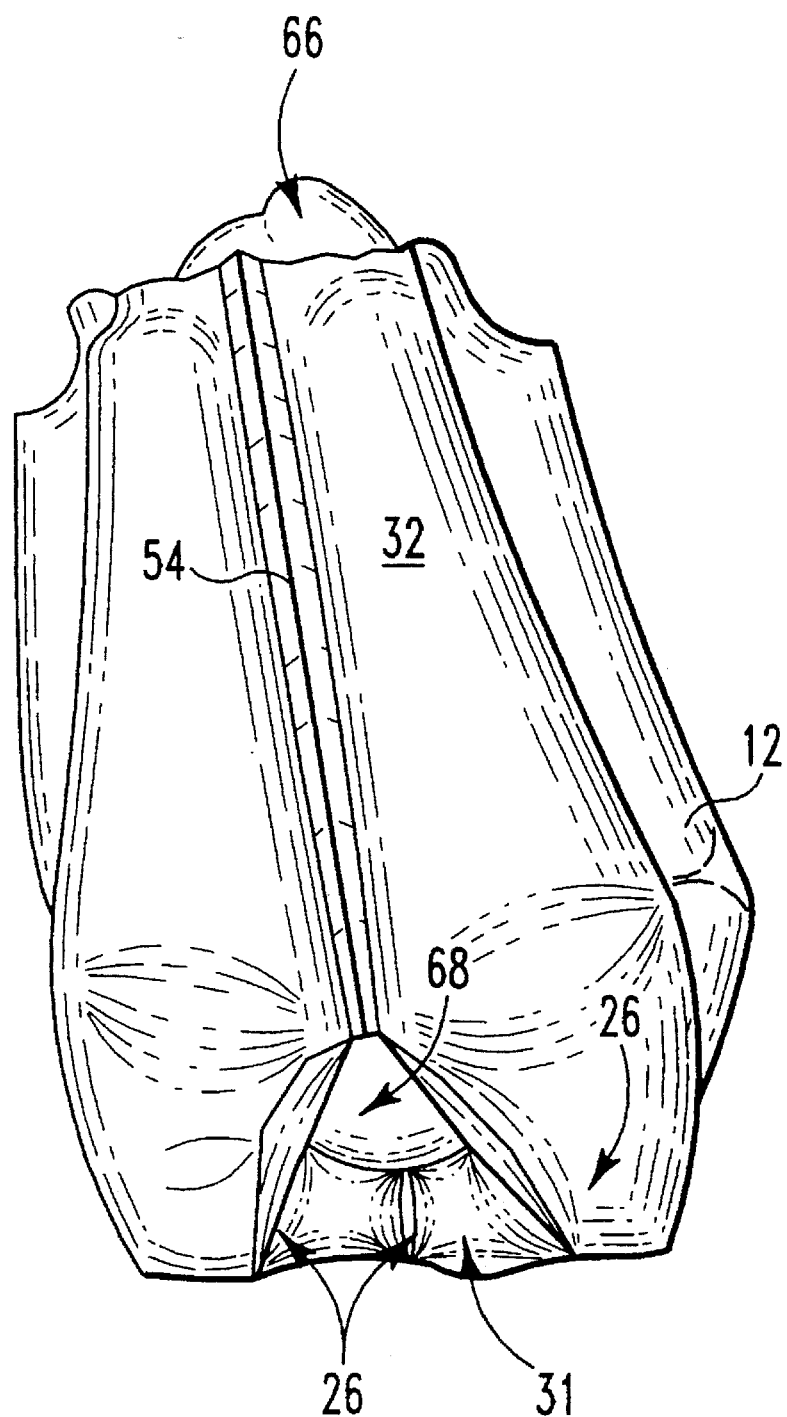
FIG. 11 is a perspective of the device while in use as viewed from the bottom of FIG. 8.

Intermediate portion 30 can further include a cut-out portion 31 integrally formed therein for receiving therein the heel of the foot (see FIGS. 7 and 11). Cut-out portion 31 allows for total suspension of the heel thereby creating zero pressure, shear, heat, moisture and bacterial effects on the heel area. This is vitally important because the heel area is the primary area of ulcer formation and treatment, particularly for elderly patients.

In use, protective device 10 is preferably disposed in an underinflated state about the lower limb and then inflated to allow its interior surface to engage and conform to the contour of the lower limb to apply an even and low interface pressure to the limb while achieving a maximum surface area contact between the interior surface and the lower limb, the benefits of which are discussed further below.

Inflatable member 12 can include a pair of sheets, an exterior or outwardly facing sheet 17 and an interior or inwardly facing sheet 19 (only sheet 17 is shown in FIG. 1) joined peripherally together forming the single air chamber therebetween. Interior and exterior sheets 17 and 19 are preferably constructed of plastic and have substantially identical configurations and are adjoined at their peripheries by conventional plastic welding methods.

The protective device 10 of the invention can include means for preventing bacterial growth, for providing visibility of the body extremity and for providing cooling, preferably comprising openings located in the inflatable member and formed at the closure. Sheets 17, 19 can, for example, have a plurality of aligned openings such as holes 24 extending therethrough with the sheets 17, 19 being joined together by heat sealing means about the circumference of each hole 24 in an airtight fashion. Device 10 can further include one or more additional ventilation openings such as a slot 25 to provide ventilation to the Achilles region of the limb when the device is secured thereabout. Openings 24 and 25 act to dissipate heat and moisture and provide air flow therethrough, allow palpation of the lower limb for edema (swelling), allows palpation and auscultation of the posterior tibial artery pulse, and provides visibility allowing a care giver to generally view the lower limb therethrough. Without heat and moisture dissipation and proper ventilation, continuously wearing device 10 for extended periods of time can become extremely uncomfortable for the patient. By providing ventilation, these openings assist in keeping the lower limb substantially dry and eliminate problems normally associated with the maceration of skin and soft tissue due to continuous high moisture and heat levels, as well as prevent bacterial growth associated with moisture and heat build-up in unventilated areas.

Protective device 10 can further include a continuous extension air bladder portion 42 affixed to the forward edge of one side of the upper portion of inflatable member 12. As shown in FIG. 1, bladder portion 42 can be affixed to a forward edge of one side 14 of upper portion 28 at region 46. When a lower extremity is cradled within the device 10, bladder portion 42 is foldable over the shin area of the lower extremity toward the opposing side 13 of upper portion 28. Space permitting, the outer edge 44 of bladder 42 may be tucked under the opposing forward edge of side 13 and straps 35 then pulled thereover and secured. Bladder portion 42 can include one or more openings 24a a integrally formed therein to perform substantially the same functions as openings 24 provided in inflatable member 12.

Bladder portion 42 may be an entirely separate air chamber and carry its own air valve so that it is separately inflatable, or bladder 42 may have a permanent internally pressurized air chamber having a static volume that is formed during its manufacture, in which case region 46 would not provide any air communication between the internal air chambers of inflatable member 12 and bladder portion 42. In a preferred embodiment, region 46 can provide air communication between inflatable member 12 and bladder portion 42 so that their respective air chambers collectively define a single air chamber inflatable via valve 20 as represented by phantom lines in FIG. 1.

Figure 4:
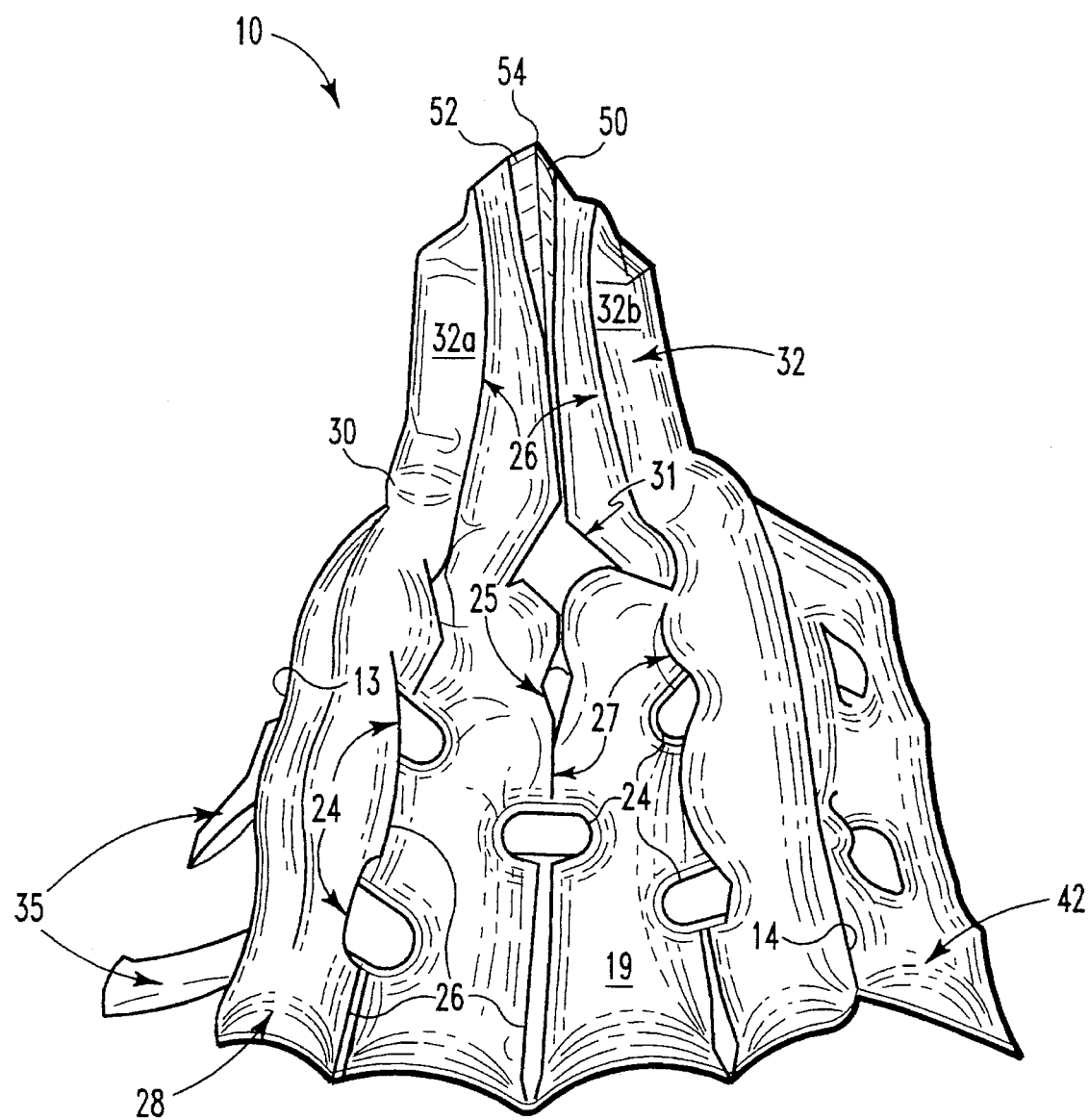
FIG. 4 is a top perspective view of the protective device in a fully assembled inflated state.

Means for releasably securing protective device 10 about the lower extremity can include one or more straps 35 attached to first side 13 of upper portion 28 as best shown in FIGS. 1 and 4. In use, straps 35 are intended to be pulled over the shin area of the calf region and releasably secured at their distal ends to the opposing second side 14 of upper portion 28. A suitable means for securing the distal ends of straps 35 to second side 14 is hook-and-loop type (VELCRO®) fasteners wherein each strap 35 carries adjacent its distal end hook fasteners 37 (shown in phantom lines in FIG. 1) and a corresponding number of loop receivers 39 are affixed to second side 14 along region 46 for releasably receiving hook fasteners 37 carried by straps 35 to secure the protective device 10 about the lower limb. Hook fasteners 37 are attached along a continuous portion of each of the straps 35 to allow a variable range of adjustability about the lower limb.

The VELCRO® closure means provided by this invention also serves as a pressure relief safety system in that in the event of acute lower limb swelling, the fasteners will pull or come apart thereby preventing the possibility of the device having a tourniquet effect on the swelling limb. Such a phenomenon can occur in the event of a blood clot forming in the limb or from congestive heart failure. The releasable securing means thus allows for easy "put on" and "take off" of the device 10 and facilitates the changing process of any medical dressings applied to the lower limb, allows for minor adjustments in the degree to which the device is secured about the lower limb (i.e., tighter or looser) without the care giver having to add or subtract air from within the inflatable member 12, and allows for quick one-handed peel-away release in emergency situations. Such securing means further allows arthritic or handicap patients to adjust the protective device 10 themselves inasmuch as there are no fine motor skills or movements required in securing or releasing device 10 to and from the lower limb.

Such securing means also eliminates the need for extra buttons or straps for securing the device, such as those used in the prior FOOT WAFFLE® device, which are often lost during use and are burdensome to medical care givers and particularly to arthritic or handicap patients who may have reduced fine motor skills. The FOOT WAFFLE® device has no pressure relief safety feature as it is secured with straps and buttons. In the event of acute swelling of the lower limb, the device of Ehob has a tourniquet effect on the limb compromising, and possibly even stopping, the blood flow to the lower limb, which can naturally have disastrous results inviting the onset of gangrene and requiring possible amputation.

The securing means further allows the protective device 10 to be custom fitted to the specific dimensions of patients' lower limbs having varying shapes and sizes, thereby eliminating many sizing difficulties and reducing inventory concerns. As noted above, the customization of the fit of device 10 to lower extremities of various shapes and sizes can additionally be achieved by the degree of inflation of the inflatable member 12; that is, air may be added to or released from inflatable member 12 via valve 20 to further custom fit the device 10 to the lower extremity.

Securing straps 35 are preferably attached to inflatable member 12 at region 48 adjacent side 13. Regions 46 and 48 adjacent sides 14 and 13, respectively, can define uninflatable areas where exterior and interior plastic sheets 17, 19 are welded or fused together to provide a strong foundation to which the various elements, i.e., straps 35, bladder 42 and loop receivers 39, may be anchored. Conventional plastic welding methods can be employed to affix straps 35 to region 48 and affix bladder portion 42 to region 46. Hook fasteners 37 and loop receivers can be adhered to member 12 using a conventional adhesive suitable for use with a vinyl plastic material from which, as discussed below, device 10 is preferably constructed.

FIG. 4 is a top perspective view of protective device 10 in an inflated and partially open state for observation purposes. In a fully assembled state, the left lower foot portion 32a of device 10 is folded inwardly in the direction of reference arrow "a" as shown in FIG. 1 and right lower foot portion 32b is likewise folded inwardly in the direction of reference arrow "b" until the interior surfaces of non-inflated bottom margins 52 and 50 of lower foot portion 32a and 32b, respectively, abut one another, at which point they are fused together to form a lower seam 54 (FIG. 4) and impart the boot-like form to protective device 10.

Figure 8:
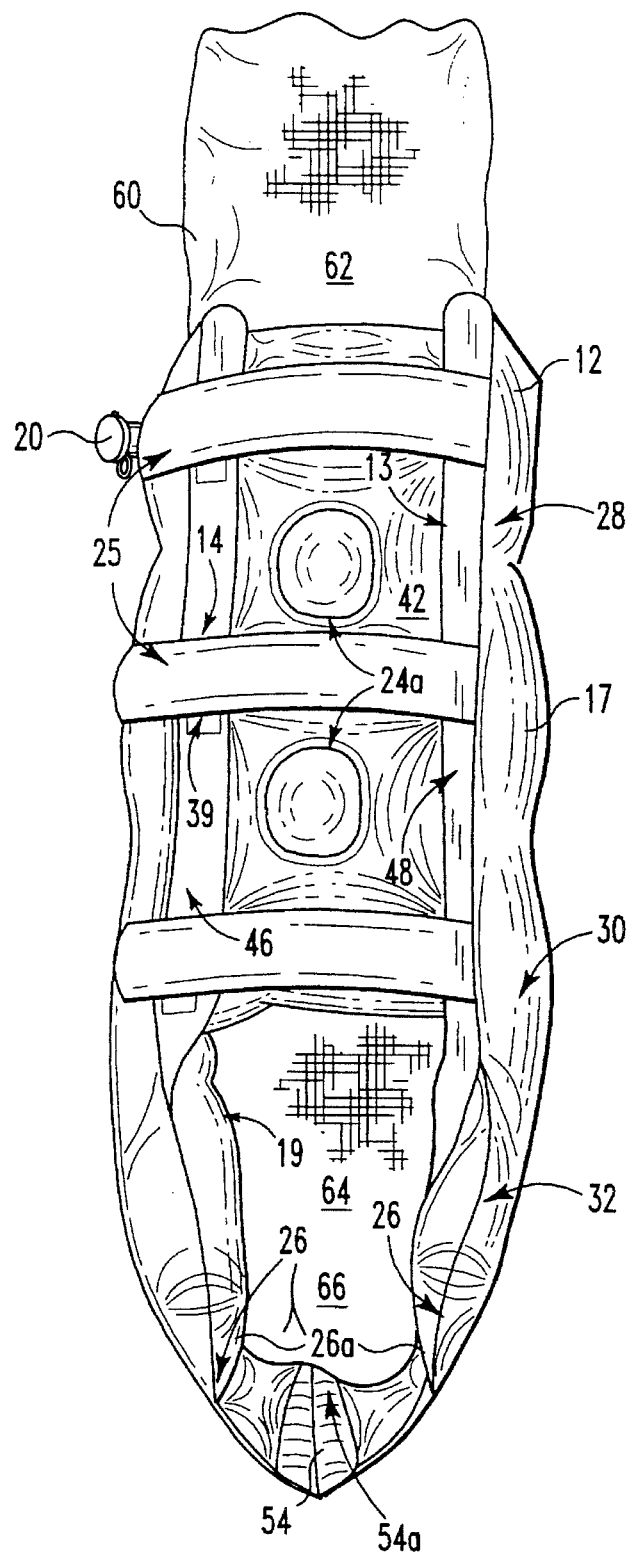
FIG. 8 is a front perspective of the inflated device of FIG. 4 operably secured about a human lower extremity.
Figure 9:
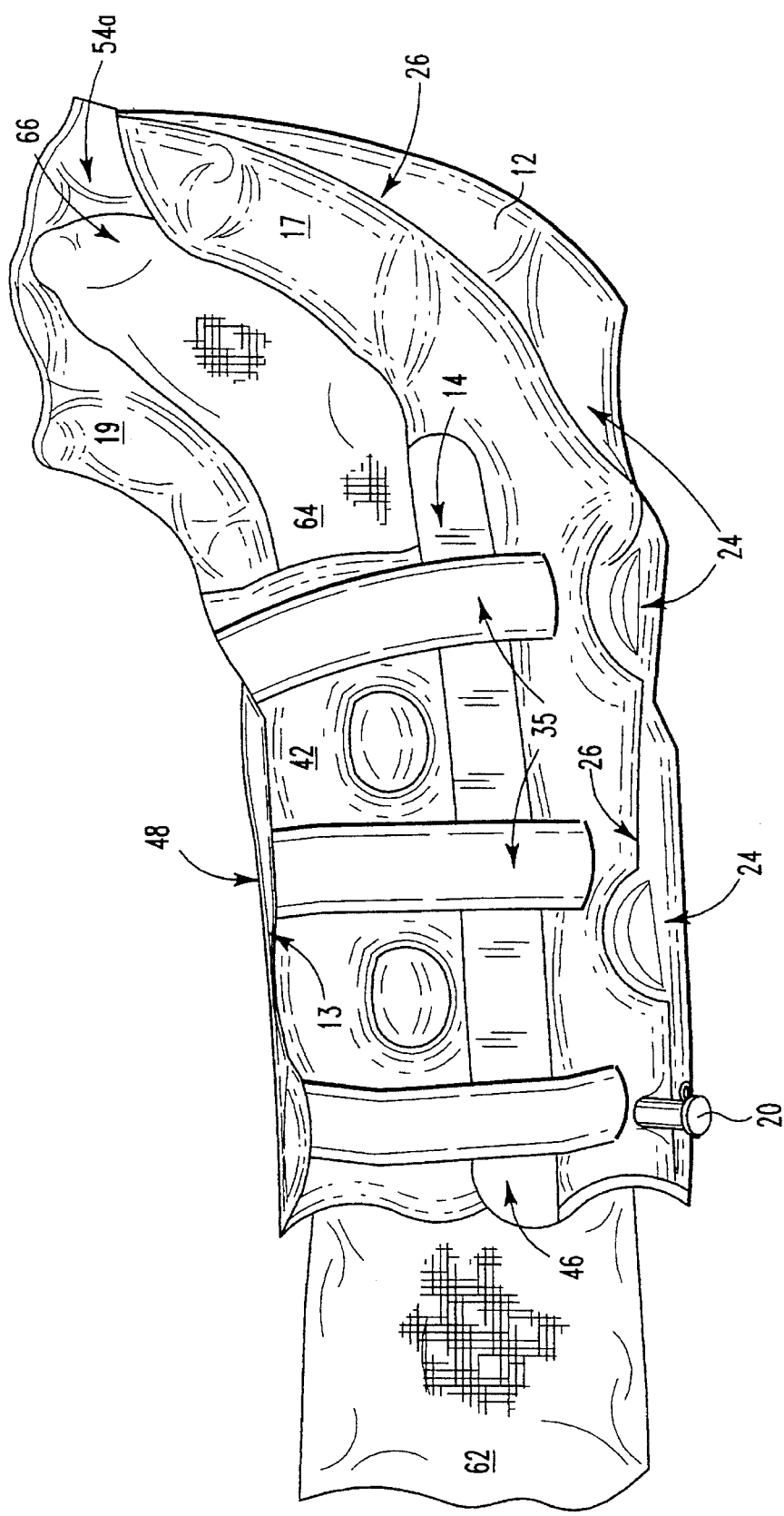
FIG. 9 is a perspective view of the device while in use as viewed from the left of FIG. 8.
Figure 10:
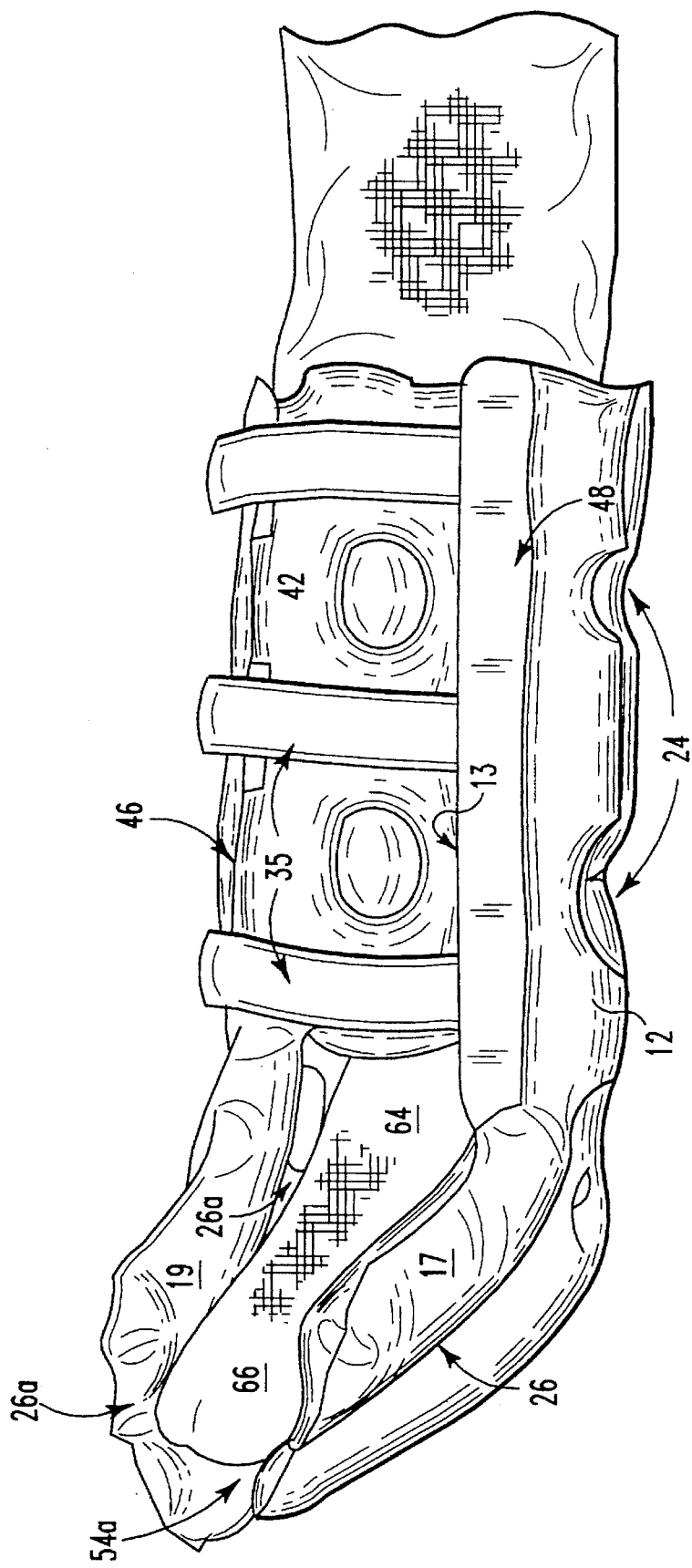
FIG. 10 is a perspective view of the device while in use as viewed from the right of FIG. 8.

Inflatable member 12 further includes a plurality of seams 26 which are formed by heat sealing the sheets 17, 19 together along preselected linear areas to thereby define a tuft-like seam. Seams 26 divide the air pressurizable chamber of member 12 into adjacent compartments in fluid communication with each other through open air channels 27 (best shown in FIG. 1) provided throughout the interior air chamber to thereby define a single-chambered inflatable device. As seen in FIGS. 8–10, tuft-like seams 26 enhance the ability of device 10 to produce a cradling effect whereby interior surface 19 can better engage and fully conform to the contour of the lower extremity.

Seam 26 immediately adjacent opening 25 combines with opening 25 and cut-out portion 31 to gently and securely fit about the heel and Achilles regions to dissipate all forces acting thereon. Said seam 26 and opening 25 are specifically located and dimensioned to insure no direct pressure is exerted on the Achilles tendon by providing minimal gradients and a smooth transition of non-support areas to support areas, thereby transferring the support pressure for this area to the gastrocnemius (calf) muscle and secondarily to the soleus muscle. These muscles, having more tissue fluids and better vascular supply, are not as susceptible to pressure breakdown.

Figure 5:
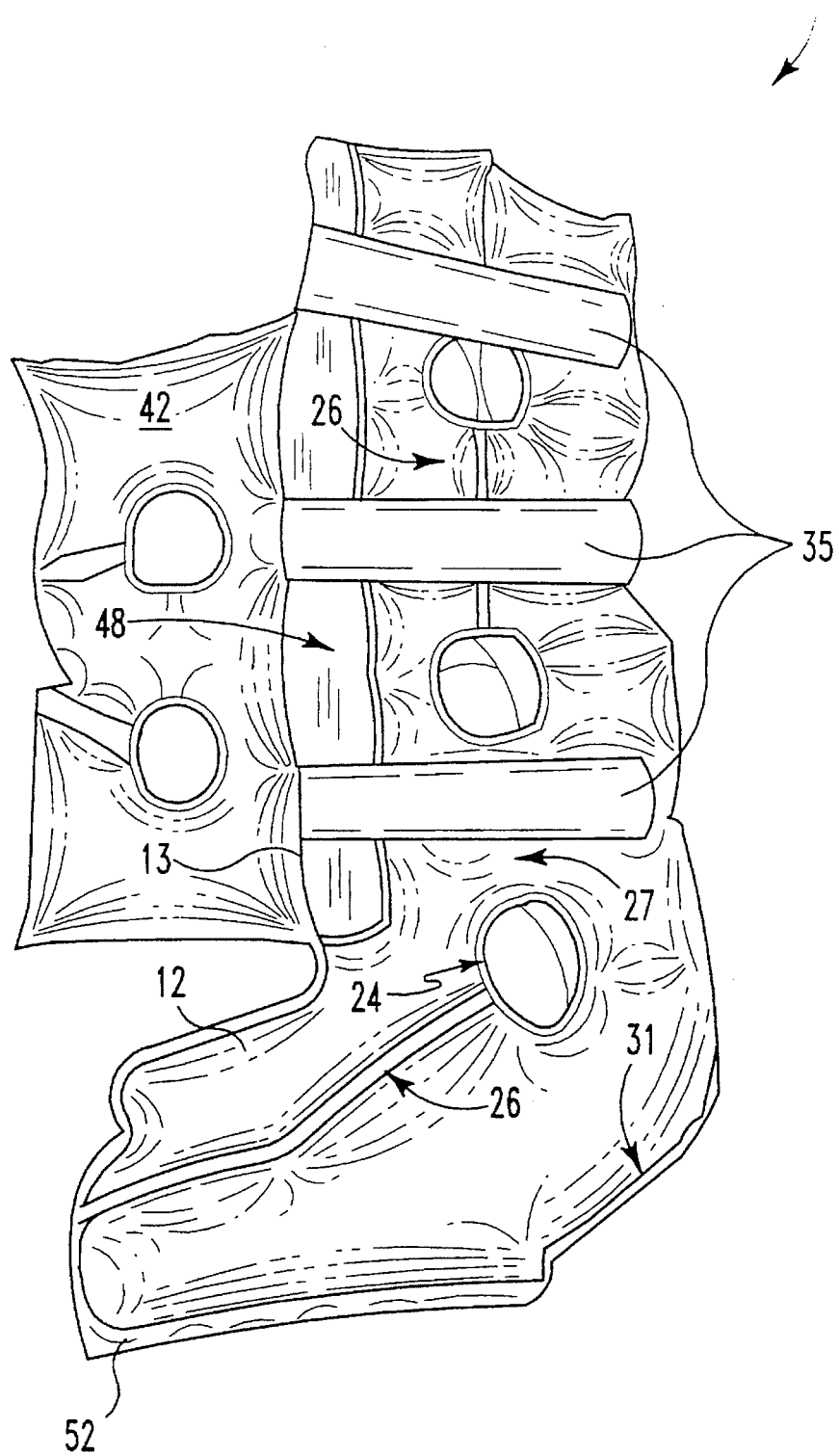
FIG. 5 is a side plan view of the inflated device of FIG. 4 with a left portion of the device as seen in FIG. 4 laid over upon the right portion in a partially closed fashion.

FIG. 5 is a side plan view of the inflated device 10 of FIG. 4 with the separate bladder portion 42 in the background of FIG. 5 and the plurality of straps 35 affixed adjacent edge 13 of the device in the foreground. The cut-out portion 31 integrally formed in the intermediate ankle portion of member 12, the seams 26 and open channel 27 formed in lower foot portion 32a can be seen in FIG. 5.

Figure 6:
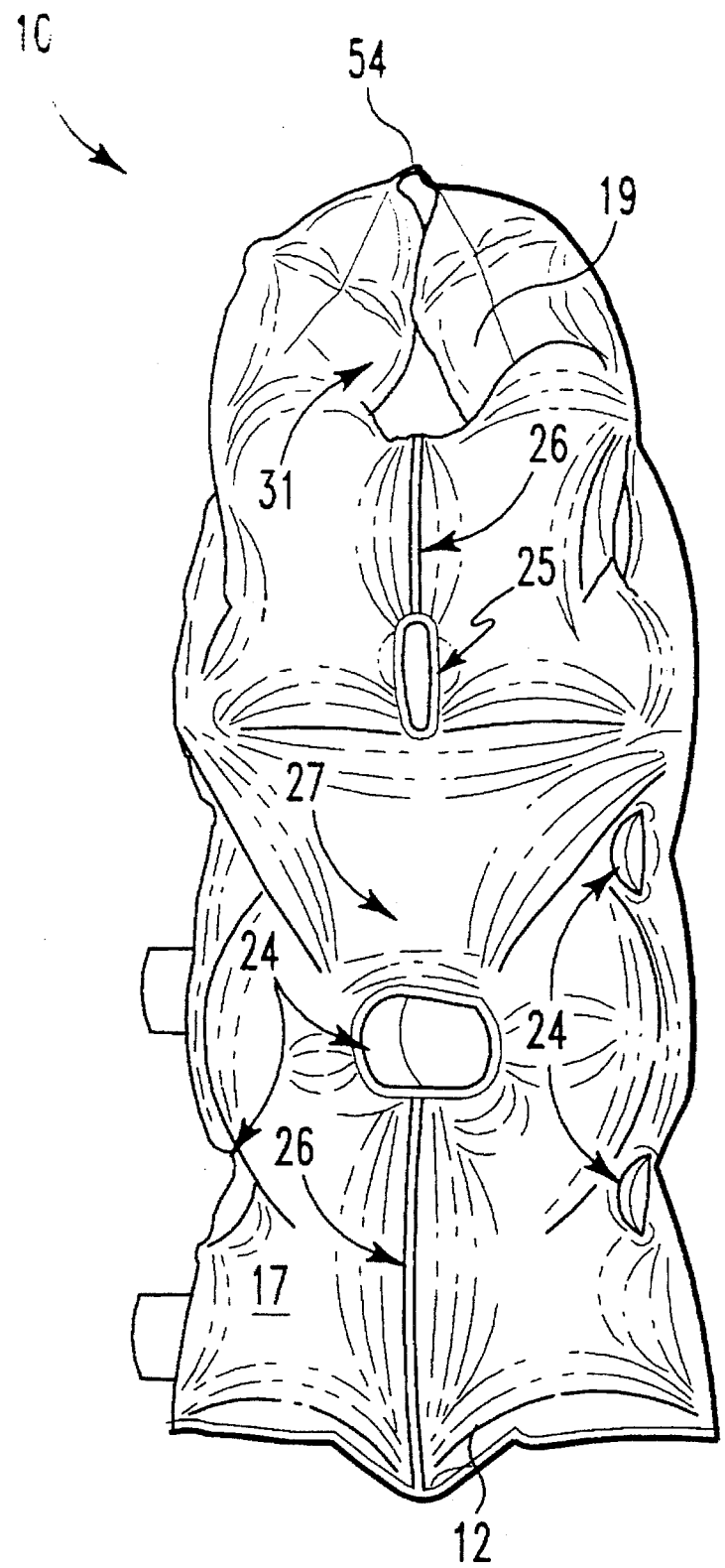
FIG. 6 is a rear perspective view of the inflated device of FIG. 4.

FIG. 6 is a rear perspective view of the inflated device of FIG. 4 while partially closed showing the cutout portion 31 for receiving the heel, ventilation opening 25 for providing air communication and dissipating heat and moisture therethrough for the Achilles region of the lower limb, and the plurality of openings 24. FIG. 6 also depicts how the seams 26 combine with openings 24 to provide a plurality of tufts and pillow-like surfaces all about device 10.

FIG. 7 is also a rear perspective view of the inflated protective device 10, but presents an isolated enlarged view angled somewhat more from the bottom of device 10 showing the heel-receiving cutout portion 31 formed in intermediate portion 30 of member 12, along with the bottom seam 54 formed by the joining or fusing together of bottom tab portions 50 and 52. The contrast in the surface topography of surfaces 17 and 19 at open channel portions 27 as compared to at tuft-like seams 26 are clearly visible in FIG. 7.

FIGS. 8–11 show a human lower extremity 60 cradled and secured within protective device 10 while in an inflated and secured state. FIG. 8 is a front perspective view and FIGS. 9 and 10 are right and left perspective views, respectively, of the inflated device 10 operably secured to lower extremity 60 which includes a calf 62, an ankle 64 and a foot 66. As shown in FIGS. 8–10, once the lower limb 60 is cradled within the protective device 10, the device is inflated and the bladder 42 is folded over the forwardly facing shin portion of calf 62 and straps 35 are thereafter pulled over the bladder 42 and secured to loop receivers 39 disposed along side 14. Seams 26 disposed in the lower portion 32 of member 12 can be seen in FIG. 8 contouringly fitting about foot 66 to provide a snug protective engagement. Visibility through to the shin portion of calf 62 is provided by visualization and ventilation holes 24a provided in bladder 42.

As may be distilled only from viewing device 10 as shown in an operable mode in FIGS. 8–11, adjacent each seam 26 and bottom seal 54 are open air channels 26a and 54a, respectively, where interior surface 19 does not engage the limb. Channels 26a and 54a assist in enabling the interior surface 19 to better conform to the contour of the limb but also perform a heat and moisture dissipation function by channeling heat and moisture away from the surface of the lower limb and through channels 26a and 54a to the ambient.

FIG. 11 is a bottom perspective view of inflatable member 12 looking directly at the bottom of lower portion 32 where bottom seam 54 is clearly shown extending from the cutout portion 31 continuously to the front of lower portion 32, beyond which the toes of foot 66 extend slightly. Seams 26 provided in member 12 enable the device to take on a low profile as shown in FIG. 11 when the patient is in a supine position which reduces the extent of hip and knee rotation and extension while still providing total suspension for the lower limb and heel, thereby eliminating virtually all forces which may adversely affect the limb and the blood circulation to its soft tissues. For the purposes of this disclosure, the terminology "low profile" is intended to mean that the portion of the device 10 (referenced 32c in FIG. 11) disposed between the limb and the underlying surface is compressed because of the low internal pressure and consequently has a thin cross-section which results in the limb being elevated above the bed only a short distance. Elevating the limb to any greater extent causes increased hip and knee rotation and extension when the patient turns his torso (rolls in bed), which is undesirable, particularly with patients having fragile joints. To this end, the single chamber nature of member 12 allows the fluctuation of the interior air volume of the static air chamber that occurs as the patient moves his lower limb about and acts to displace the interface pressure evenly throughout inflatable member 12.

Protective device 10 and its components are preferably constructed of a high grade medical vinyl material that is bacteria-static, odorless and flame retardant. Plastic is preferred because it is readily deformable and enhances the ability of the device 10 to conform to the contour of the limb. The bacteria-static nature of the material helps prevent infection. The fire retardant nature of the material naturally enhances its safety. Further, it is preferred that the material be odorless to cause no discomfort to a patient who may be allergic or hyper-sensitive to smells or odors, particularly due to their medical condition. A suitable medical vinyl material must also be easily cleaned and free of bacteria-friendly areas to assist in the prevention of bacteria growth. Such a preferred medical vinyl is polyvinyl chloride.

Polyvinyl chloride provides a strong yet flexible construction to device 10 which allows it to be used in conjunction with other products such as sequential pressure cuffs for various dressings and positions. Polyvinyl chloride is also inexpensive rendering protective device 10 very affordable and cost efficient. Furthermore, being deflatable and flexible, protective device 10 avoids the bulky appearance of similar prior art products and is subject to compact packaging, storage and distribution. These are all considerations which are important in today's cost-conscious medical field.

Figure 3:
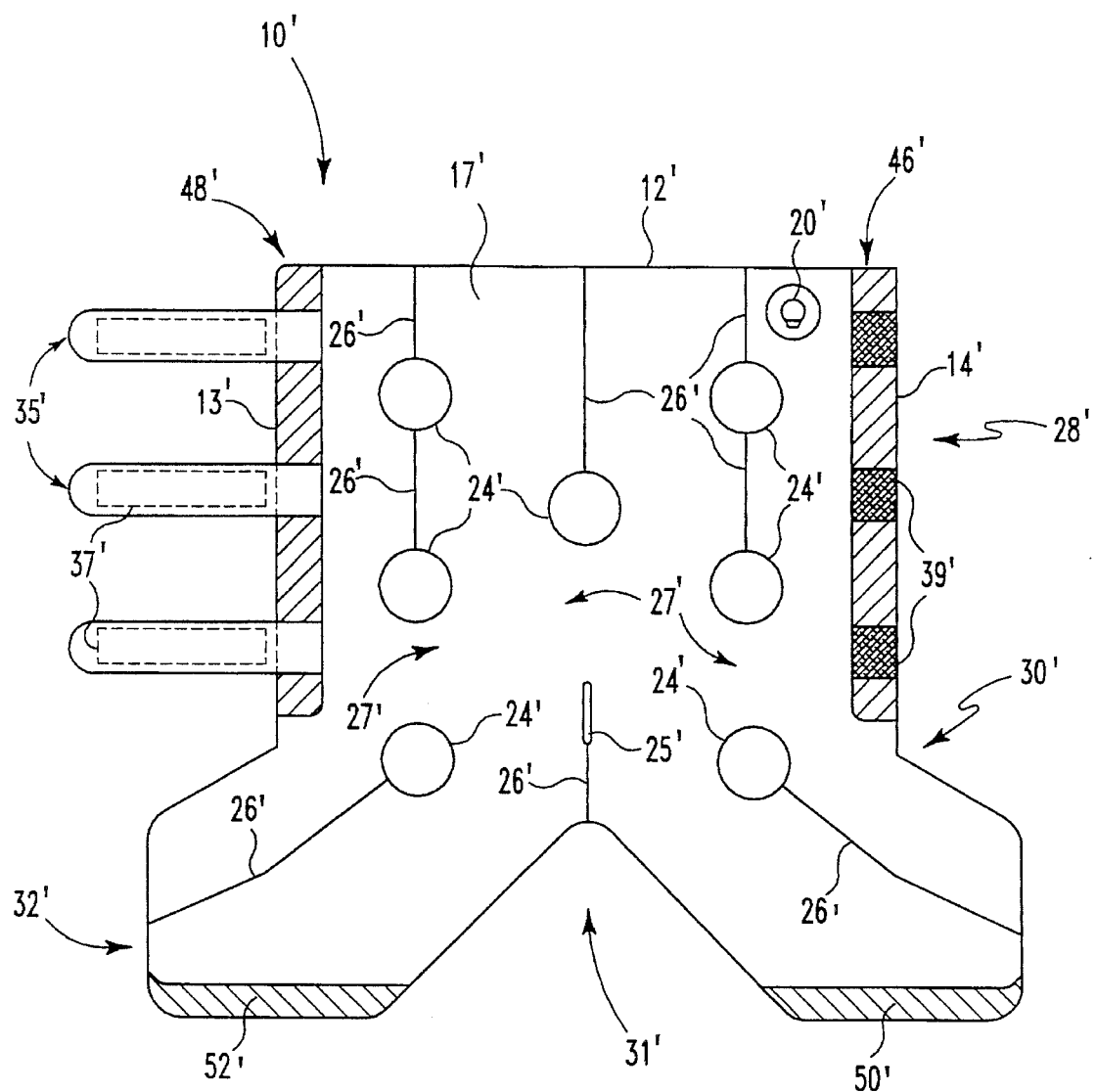
FIG. 3 is a flat plan view of a further embodiment of a protective device provided by this invention also shown in an underinflated, unassembled state for purposes of illustration.

A further embodiment of a protective and pressure normalizing device 10' provided by this invention is shown in FIG. 3. Device 10' is substantially similar to its brother embodiment shown in the remaining figures, particularly FIG. 1, wherein the only difference is that device 10' of FIG. 3 does not include an extended bladder portion such as bladder 42 shown in FIG. 1. Accordingly, the elements of device 10' in FIG. 3 are numbered similar to their corresponding elements in FIG. 1.

A method is further provided by this invention of protecting a human limb and normalizing the forces acting thereon, comprising generally providing an air pressurizable device 10 in an underinflated state and arranging the device about an extremity in a cradle-like fashion, inflating the device 10 to the extent so that it engages and conforms to the contour of extremity 60, and securing the device 10 about the extremity 60. Alternatively, the device 10 can be arranged and secured about the limb in an underinflated state and then inflated to the desired fit. Device 10 generally includes an inflatable member 12 including a pair of plastic sheets 17, 19 joined peripherally together forming a single-chambered static air inflatable chamber 12, means for releasably securing the member 12 to the extremity 60, and valve means 20 carried by member 12 operable to allow inflation of member 12 to a desired internal pressure.

This invention further provides a method of maintaining or improving the blood flow circulation to the soft tissues of a lower extremity to prevent the formation and to aid in the healing of pressure sores, generally comprising providing an inflatable device 10 in an underinflated state and arranging it about a limb 60 in a cradling manner, pressurizing the device until its interior surface engages and snugly conforms to the contour of the limb 60, and securing the device about the extremity with releasable means.

The single chamber static air design of protective device 10 allows for a true low pressure system that cannot be duplicated by a device having multiple interior inflation chambers. Such multi-chambered devices are unable to achieve the uniformity of overall interface pressure applied by the device to the limb to the extent accomplished by this invention because of the inability of multi-chambered devices to displace the increased pressure that may exist at one point evenly throughout the device through the displacement of the internal air volume within the device. Such is not possible in a multi-chambered device where, for example, undue pressure can be exerted by a separate air chamber disposed in the foot region, and as a result of its contained pressure, cannot be normalized as in the invention through displacement of the interior air volume from that region to, for example, the upper calf region, which is an area having greater vascular supply less prone to breakdown. The device 10 of this invention permits displacement of the internal air volume in member 12 and ensures both proper inflation of the device as well as total suspension of the limb and heel, thereby removing the uncertainly that often accompanies inflatable products used in a medical settings and increasing the confidence and comfort of both the medical care giver and the patient.

Thus, the low internal static air pressure of single-chambered device 10 and its method of use provided by this invention dissipates undue pressures and evenly distributes the pressures and forces between device 10 and extremity 60 and the effect of gravity (i.e., the weight of the limb itself) by enabling the interior surface 19 of device 10 to conform to the contour of limb 60, thus increasing the surface area contact between interior surface 19 and limb 60, which in turn reduces the interface pressure at any one point. Such interface pressure may additionally be regulated by the extent of the inflation of member 12 and the extent to which the securing means is tightened or loosened, including the extent to which the individual straps 35 are tightened or loosened relative to each other.

The low internal static air pressure of member 12 further reduces the tangential pressures applied by the member 12 against the calf, Achilles tendon, heel, ankle and foot regions of limb 60. The increased surface area contact between interior surface 19 and the limb 60 consequently reduces the tendency of the limb to slide longitudinally or rotationally relative to the device 10 while secured therein, which in turn reduces the tendency of pressure sores to form. Moreover, the general construction of member 12 and the combined effect of openings 24, 25 and tuft-like seams 26 will tend to further restrict longitudinal and rotational movement of the lower limb by essentially folding up and around the limb to cradle it. The even distribution and dissipation of the forces acting on the lower limb further acts to maintain a sufficient blood flow throughout the soft tissues of the extremity which acts to prevent the formation of pressure sores and other medical pathologies and to assist in the healing of any such pathologies already formed.

Accordingly, this invention provides an effective pressure relief system that raises the level of comfort for the patient by adapting and contouring to the limb to provide total equalized support and pressure normalization to the entire limb, thereby providing a cost effective solution to the problem of pressure sore prevention and management.

While the device and method described above constitutes a presently preferred embodiment, the invention can take many other forms. Accordingly, it should be understood that the invention is to be limited only insofar as is required by the scope of the following claims.

We claim:

1. A protective and pressure normalizing device for a body extremity, comprising:

an inflatable member forming a single-chambered static pressure chamber, said inflatable member having an exterior surface, an interior surface, an upper portion for partially enclosing an upper region of the extremity, an intermediate portion for partially enclosing an intermediate region of the extremity, and a lower portion for partially enclosing a lower region of the extremity;

means for releasably securing the inflatable member about said lower extremity;

valve means for inflating said member to a desired internal pressure; and an air bladder affixed to a forward edge of one side of the upper portion of said inflatable member, and being foldable toward a forward edge of an opposing second side of the upper portion of said inflatable member;

said valve means being operable to inflate said member after the member is positioned about the lower extremity while in an underinflated state so that said member engages and partially encloses in a cradling fashion the extremity and applies a uniform interface pressure thereto, said securing means being disposed over said air bladder when in the secured position.

2. The protective and pressure normalizing device as in claim 1 wherein said exterior and interior surfaces include a plurality of aligned openings extending therethrough with said exterior and interior surfaces being joined together about the circumference of each said opening.

3. The protective and pressure normalizing device as in claim 2 wherein said openings are located for providing visibility therethrough to the extremity.

4. The protective and pressure normalizing device as in claim 2 wherein said openings are located for dissipating heat and moisture therethrough.

5. The protective and pressure normalizing device as in claim 1 wherein said member normalizes the pressure acting on the extremity by displacing the interior air volume of said member from areas of high pressure to areas of low pressure.

6. The protective and pressure normalizing device of claim 1 wherein said means for releasably securing the inflatable member about the extremity includes hook-andloop fastening means adapted to detach in the event of acute edema of the extremity.

7. The protective and pressure normalizing device of claim 6 wherein said upper region comprises a calf region, wherein said inflatable member encloses the rear and side portions of said calf region leaving a forwardly facing shin portion exposed, and wherein said hook-and-loop fastening means includes one or more straps carrying hook fasteners thereon, said straps extending from a first side of said member over the exposed shin portion to a second opposing side of said member, said second opposing side carrying loop receivers for detachably receiving the hook fasteners of said straps.

8. The protective and pressure normalizing device of claim 1 wherein said intermediate region comprises an ankle and heel region, and wherein said intermediate portion includes a cut-out portion for receiving therein the heel of the extremity.

9. The protective and pressure normalizing device of claim 1 wherein said securing means comprises hook-and-loop fastening means including one or more straps attached to a first side of the upper portion, each said strap having a hook fastener affixed thereto, and a corresponding number of loop receivers affixed to a second opposite side of the upper portion for releasably receiving the hook fasteners of said straps, and wherein said air bladder is foldable over an exposed shin area of the extremity and said one or more straps are then pulled thereover and releasably secured to said loop receivers.

10. The protective and pressure normalizing device of claim 1 wherein said inflatable member has a low internal static air pressure of less than about 0.5 p.s.i.

11. The protective and pressure normalizing device of claim 1 wherein said low internal static air pressure of said inflatable member dissipates and evenly distributes the interface pressure between said device and said extremity.

12. The protective and pressure normalizing device of claim 11 wherein the interface pressure between the interior surface of said member and the surface of the extremity is regulatable by the extent of inflation of said inflatable member.

13. The protective and pressure normalizing device of claim 11 wherein said low internal static pressure of said single-chambered member comprises means for allowing said inflatable member to conform to the contour of the extremity increasing the surface area contact therebetween and reducing the interface pressure therebetween.

14. The protective and pressure normalizing device of claim 11 wherein the even distribution of said interface pressure prevents the compromising of blood flow circulation to the soft tissues throughout the extremity.

15. The protective and pressure normalizing device as in claim 11 whereas the inflation of said member and the conforming of its interior surface to the extremity comprise means for reducing tangential pressures therebetween.

16. The protective and pressure normalizing device as in claim 11 wherein the inflation of said member and the conforming of its interior surface to the extremity comprises means for increasing the interface contact therebetween and reducing the relative movement of the extremity while secured within said device.

17. The protective and pressure normalizing device of claim 1 wherein said device is capable of being custom fitted to extremities having varying shapes and sizes by the degree of inflation of said inflatable member.

18. The protective and pressure normalizing device of claim 1 wherein said inflatable member is constructed of a bacteria-static, odorless and flame retardant material.

19. A protective and pressure normalizing device for a human lower leg, comprising:

an inflatable member forming a single-chambered static pressure chamber, said inflatable member having an exterior surface, an interior surface, an upper portion for engaging an upper region of the lower leg including generally the gastrocnemius area of the leg, an intermediate portion for engaging an intermediate region of the lower leg including generally the Achilles tendon and ankle region, and a lower portion for engaging a lower region of the lower leg including the foot region;

a plurality of seams joining together said exterior and interior surfaces dividing the interior of the pressure chamber into a plurality of intercommunicating compartments, one of said plurality of seams being positioned within the intermediate portion of said member so as to, when said member is secured about the leg, oppose the Achilles tendon area for preventing pressure caused by the weight of the leg from being imparted to the Achilles tendon area while in a supine position;

means for releasably securing the inflatable member about the lower leg and foot; and valve means for inflating said member to a desired internal pressure, said valve means being operable to inflate said member after said member is positioned about the lower leg and foot while in an underinflated state so that said member engages and partially encloses in a cradling fashion the lower leg and foot and applies a uniform interface pressure thereto while preventing undue pressure from being imparted to the heel or Achilles tendon areas of the lower leg.

20. An air pressurizable supporting device adapted to cradle and conform to the contour of a lower limb for improving blood flow to the soft tissues thereof, comprising:

an inflatable wrap having a single internal air chamber and including an interior sheet and an exterior sheet joined peripherally together forming said single air chamber therebetween, nozzle means for admitting air into said single air chamber, an upper portion for engaging and partially enclosing the shin and calf region of the lower limb, an intermediate portion for engaging and partially enclosing the ankle and Achilles region of the lower limb, said intermediate portion having a cut-out portion integrally formed therein for receiving a heel, a lower portion for engaging and partially enclosing the foot region of the lower limb, a forward air bladder affixd to a forward edge of one side of the upper portion of said wrap and foldable toward a forward edge of an opposing second side of said upper portion for covering the anterior shin portion of the lower limb, and means for releasably securing the inflatable wrap about said lower limb after said forward air bladder has been disposed over the anterior shin portion, said sheets having a plurality of aligned holes extending therethrough for dissipating heat and moisture and admitting air therethrough, said sheets being joined around the circumference of each hole, said wrap being inflatable when disposed in an underinflated state about said lower limb to allow the interior surface of said wrap to engage and conform to the contour of said lower limb to maximize the interior susrface area in contact with the lower extremity and apply a uniform pressure at the interface between the interior surface and the lower limb.

21. The supporting device of claim 20 wherein said wrap has, while in an inflated state secured about said lower limb, a low profile reducing the extent of hip and knee rotation and hip and knee extension while the wearer is disposed in a supine position.

22. The supporting device of claim 21 wherein the heel is suspended only slightly above a bed surface eliminating substantially all forces acting on the heel.

23. The supporting device of claim 20 further comprising an opening formed integrally in the central portion of said inflatable wrap for providing ventilation and pressure dissipation to the Achilles region of said lower limb.

24. The supporting device as in claim 20 wherein said member is deflatable for compact packaging, storage and distribution.

25. A method of protecting and normalizing the pressure and forces acting on a human lower limb comprising the steps of:

providing an air pressurizable device in an underinflated state;

arranging said device about a lower limb in a cradle-like fashion, said device having an interior surface and an exterior surface;

inflating said device to the extent that the interior surface of said device engages and conforms to the contour of the limb; and securing the device about the lower extremity, said device comprising:

an inflatable chamber forming a single-chambered static air inflatable member, said inflatable member having an upper portion for partially enclosing an upper region of the limb, an intermediate portion for partially enclosing an intermediate region of the limb, and a lower portion for partially enclosing a lower region of the limb;

means for releasably securing the inflatable member about the limb;

valve means for inflating said member to a desired internal pressure; and an air bladder extension affixed to a first side of the upper portion of said inflatable member, said air bladder being foldable over toward an opposing second side of said upper portion prior to said securing means being operatively secured over said air bladder.

26. The method of claim 25 wherein said inflatable member has a plurality of aligned openings integrally formed in the interior and exterior surfaces thereof with said interior and exterior surfaces being joined together about the circumference of each said opening.

27. The method of claim 25 wherein said means for releasably securing the inflatable device about the limb includes hook-and-loop fastening means.

28. The method of claim 25 wherein said limb is a lower extremity including a forwardly facing shin, wherein said arranging step includes enclosing the rear, bottom and side portions of the lower extremity within the device and folding the forward air bladder over the shin of the lower extremity, wherein said hook-and-loop fastening means includes one or more straps that carry hook fasteners adjacent their distal ends, said one or more straps extending from a first side of said member, and loop receivers disposed on a second opposing side of said member, and wherein said securing step includes pulling the straps over the air bladder covering the shin of the limb and releasably affixing the hook fasteners carried by said straps to the loop receivers disposed on the opposing side of said inflatable member.

29. The method of claim 25 wherein said securing step includes dissipating and evenly distributing the interface forces acting on the limb.

30. The method of claim 29 wherein said dissipating and evenly distributing the interface pressure includes regulating the extent of inflation of said inflatable member.

31. The method of claim 29 wherein said dissipating and evenly distributing the interface pressure includes maintaining a proper blood flow throughout the soft tissues of the limb for retarding the formation and aiding in the healing of pressure sores and other medical pathologies.

32. The method of claim 25 wherein said securing step includes custom fitting said device to the limb by controlling the degree of inflation of said member and the extent to which the securing means is tightened or loosened about the limb.

33. The method of claim 25 wherein the limb comprises a lower extremity and said method further includes eliminating all forces and pressures acting on the lower extremity by suspending the heel slightly vertically above a bed surface, said suspending being carried out by said inflatable device.

34. A method of maintaining or improving the blood flow circulation to the soft tissues of a human lower extremity to prevent the formation and to aid in the healing of pressure sores, comprising the steps of:

providing an inflatable device in an underinflated state;

arranging said device about a lower extremity in a cradling manner, said device having an interior surface;

securing the device about the lower extremity with releasable fastening means; and pressurizing the device until its interior surface engages and conforms to the contour of the lower extremity, said device comprising:

an inflatable member having a single internal air chamber defined by an interior sheet and an exterior sheet joined peripherally together forming said single air chamber therebetween, nozzle means for admitting air into said single chamber, an upper portion for partially enclosing an upper calf region of the lower extremity, an intermediate portion for partially enclosing an ankle and Achilles region of the lower extremity, said intermediate portion having a cut-out portion formed therein for receiving the heel of the lower extremity, a lower portion for partially enclosing the foot of the lower extremity, an air bladder affixed to a forward edge of one side of the upper portion of said inflatable member, said air bladder being foldable over toward a forward edge of an opposing second side of said upper portion, and means for releasably securing the inflatable device about the lower extremity, said sheets having a plurality of aligned holes extending therethrough for dissipating heat and admitting air therethrough, said sheets being sealingly joined together about the circumference of each said hole.

35. The method of claim 34 wherein said securing means comprises hook-and-loop fastening means including one or more straps attached to a first side of the upper portion, each said strap carrying a hook fastener affixed thereon, and a corresponding number of loop receivers affixed to a second opposite side of the upper portion for releasably receiving the hook fasteners of said straps, and wherein said securing step includes folding said air bladder over and pulling said one or more straps thereover and releasably securing said straps to said loop receivers.

36. The method of claim 34 wherein the device is capable of being custom fitted to lower extremities of varying shapes and sizes by the degree of inflation of said inflatable member and the ability to selectively adjust the securing means about the lower extremity.

37. The method of claim 34 wherein said inflating step includes imparting a low-pressure low profile to the device for reducing the extent of hip and knee rotation and hip and knee extension while the patient is disposed in a supine position.

38. A method of protecting and normalizing the pressure and forces acting on a human lower limb comprising the steps of:

providing an air pressurizable device in an underinflated state;

arranging said device about a limb in a cradle-like fashion, said device having an interior surface and an exterior surface;

inflating said device to the extent that the interior surface of said device engages and conforms to the contour of the limb; and securing the device about the lower limb, said device comprising:

an inflatable chamber forming a single-chambered static air inflatable member, said inflatable member having an upper portion for engaging an upper region of the limb, an intermediate portion for engaging an intermediate region of the limb, and a lower portion for engaging a lower region of the limb;

one or more seams partitioning the interior of the inflatable chamber into two or more intercommunicating air compartments, one of said one or more seams being positioned opposite the Achilles tendon area of the lower limb when said device is secured about the limb for cradling therein the Achilles tendon area of the limb for preventing any undue force or pressure from being imparted thereto while in a supine position;

means for releasably securing the inflatable member about the limb; and valve means for inflating said member to a desired internal pressure.

39. A method of maintaining or improving the blood flow circulation to the soft tissues of a human lower extremity to prevent the formation and to aid in the healing of pressure sores, comprising the steps of:

providing an inflatable boot-shaped device in an underinflated state;

arranging said device about a lower extremity in a cradling manner, said device having an interior surface;

securing the device about the lower extremity with releasable fastening means; and pressurizing the device until its interior surface engages and conforms to the contour of the lower extremity, said device comprising:

an inflatable member having a single internal air chamber defined by an interior sheet and an exterior sheet joined peripherally together forming said single air chamber therebetween, nozzle means for admitting air into said single chamber, an upper portion for partially enclosing an upper calf region of the lower extremity, an intermediate portion for partially enclosing the ankle and Achilles tendon region of the lower extremity, said intermediate portion having a cut-out portion formed therein for receiving the heel of the lower extremity, a lower portion for partially enclosing the foot of the lower extremity, a plurality of seams joining together said interior and exterior sheets at predetermined areas to divide the interior of said air chamber into a plurality of intercommunicating compartments, one of said plurality of seams being arranged to, when the device is secured about the limb, oppose the Achilles tendon proper for cradling the Achilles tendon proper therein and preventing any forces caused by the weight of the lower extremity from being imparted to the heel or Achilles tendon proper while in a supine position, and means for releasably securing the inflatable device about the lower extremity, said sheets having a plurality of aligned holes extending therethrough for dissipating heat and admitting air therethrough, said sheets being joined together around the circumference of each hole in a fluid-tight fashion.

* * * * *

UNITED STATES PATENT AND TRADEMARK OFFICE
CERTIFICATE OF CORRECTION

PATENT NO. : 5,489,259
DATED : February 6, 1996
INVENTOR(S) : Kerry L. Jacobs, et al.

It is certified that error appears in the above-indentified patent and that said Letters Patent is hereby corrected as shown below:

On the title page, under the heading "FOREIGN PATENT DOCUMENTS", enter -- 18,732 of 1893 United Kingdom 2/22 --

In Col. 5, line 33 before the words "integrally formed", delete --a--.

In Col. 13, line 1, "susrface" should be --surface--.

Signed and Sealed this

Twenty-ninth Day of October 1996

Attest:

BRUCE LEHMAN

Attesting Officer

Commissioner of Patents and Trademarks